(12) United States Patent
Hodgkiss et al.

(10) Patent No.: US 9,752,927 B2
(45) Date of Patent: Sep. 5, 2017

(54) TRANSIENT GRATING TIME RESOLVED LUMINESCENCE MEASUREMENTS

(71) Applicant: VICTORIA LINK LTD, Wellington (NZ)

(72) Inventors: Justin M. Hodgkiss, Wellington (NZ); Kai Chen, Wellington (NZ)

(73) Assignee: VICTORIA LINK LTD, Wellington (NZ)

( * ) Notice: Subject to any disclaimer, the term of this patent is extended or adjusted under 35 U.S.C. 154(b) by 0 days.

(21) Appl. No.: 15/117,598

(22) PCT Filed: Feb. 5, 2015

(86) PCT No.: PCT/IB2015/050884
§ 371 (c)(1),
(2) Date: Aug. 9, 2016

(87) PCT Pub. No.: WO2015/118481
PCT Pub. Date: Aug. 13, 2015

(65) Prior Publication Data
US 2016/0356644 A1 Dec. 8, 2016

Related U.S. Application Data

(60) Provisional application No. 61/938,059, filed on Feb. 10, 2014.

(51) Int. Cl.
*G01J 1/42* (2006.01)
*G01N 21/63* (2006.01)
(Continued)

(52) U.S. Cl.
CPC .......... *G01J 1/4228* (2013.01); *G01J 3/0232* (2013.01); *G01J 3/2889* (2013.01); *G01J 3/4406* (2013.01);
(Continued)

(58) Field of Classification Search
CPC .. G01J 1/4228; G01J 3/2889; G01B 9/02041; G01N 21/636
See application file for complete search history.

(56) References Cited

U.S. PATENT DOCUMENTS 5,479,256 A  12/1995  Tamai et al.
6,008,899 A  12/1999  Trebino et al.
(Continued)

OTHER PUBLICATIONS

Lee, D. et al., "Toward single-shot measurement of a broadband ultrafast continuum," J. Opt. Soc. Am. B/vol. 25, No. 6 (2008): A34-A40. Abstract, figure 1, p. A35, col. 2, lines 52-57, p. A36, col. 1, lines 15-18, 22-25, p. A37, col. 1, lines 8-11, p. A38, lines 24-27.
(Continued)

*Primary Examiner* — David Porta
*Assistant Examiner* — Faye Boosalis
(74) *Attorney, Agent, or Firm* — Polsinelli PC

(57) ABSTRACT

A transient grating (TG) is used as an optical gating element with sub-picosecond time resolution for luminescence measurements from a photo-detector array. The transient grating is formed in a gate medium by one or more pulsed gate beams. For photoluminescence measurements such as photoluminescence spectroscopy or imaging, a source is excited by a pulsed excitation beam, and the pulsed gate beams are synchronized to the pulsed excitation beam with an adjustable delay between the excitation of the source and the formation of the TG. Moreover, a source or its spectra can be imaged at two different regions of the photo-detector array at two different times spaced in time by a selected duration of time with sub-picosecond resolution over a range of a nanosecond or more. A beam from the source is deflected to the different regions by changing the frequency or geometry of the pulsed gate beams.

18 Claims, 7 Drawing Sheets

(51) Int. Cl.
    *G01N 21/64*     (2006.01)
    *G01N 21/65*     (2006.01)
    *G01J 3/28*      (2006.01)
    *G01J 3/02*      (2006.01)
    *G01J 3/44*      (2006.01)

(52) U.S. Cl.
    CPC ....... *G01N 21/636* (2013.01); *G01N 21/6408* (2013.01); *G01N 21/65* (2013.01); *G01J 2003/4424* (2013.01); *G01N 2201/061* (2013.01); *G01N 2201/0696* (2013.01)

(56) References Cited

U.S. PATENT DOCUMENTS

2006/0119855 A1   6/2006   Li
2008/0192252 A1   8/2008   Moriya et al.

OTHER PUBLICATIONS

International Search Report and Written Opinion of the International Searching Authority, PCT/IB2015/050884.

TRANSIENT GRATING TIME RESOLVED LUMINESCENCE MEASUREMENTS

RELATED APPLICATIONS

This application is a national stage application (under 35 U.S.C. §371) of PCT/IB2015/050884,filed Feb. 5, 2015, which claims priority to U.S. Provisional Application No. 61/938,059, filed Feb. 10, 2014.

TECHNICAL FIELD

This disclosure relates to the use of transient gratings as optical gates for time resolved luminescence measurements, such as time resolved photoluminescence (TRPL) spectroscopy and time resolved luminescence imaging.

BACKGROUND ART

Photoluminescence (PL) spectroscopy is an essential tool to study photo-excited electronic processes [Lakowicz, Joseph R., ed. *Principles of fluorescence spectroscopy*. Springer, 2009.]. Among various PL spectroscopy techniques, time-resolved photoluminescence (TRPL) spectroscopy has been shown to be a powerful tool to study photochemistry, photophysics and photobiology [Fleming, Graham. *Chemical applications of ultrafast spectroscopy*, (1986). Beechem, Joseph M., and Ludwig Brand, *Annual review of biochemistry* 54.1 (1985): 43-71.]. The advantages of TRPL include high sensitivity and selectivity. With careful experimental design, TRPL can be performed as a background free measurement to probe the weak interaction of the excitations. Because TRPL selectively probes emissive photoexcitations, it also provides valuable information to study complex systems that involve various excited species. In contrast to other time resolved spectroscopy techniques which are based on complex nonlinear processes, TRPL only evolves with linear interaction process between the photon and the sample. Thus, it can provide rich information about the dynamics of excited states, and the signal interpretation is straight forward.

The TRPL techniques can be classified by two classes: pulse fluorometry and phase-modulation fluorometry [Lakowicz, Joseph R., ed. *Principles of fluorescence spectroscopy*. Springer, 2009.]. The present disclosure is focused on the pulse fluorometry method. In pulse fluorometry, the sample is excited by a short laser/optical pulse. Then, the PL signal is gated by a fast optical shutter and measured as function of time. The PL can be gated electronically or optically. TRPL data contains two dimensions; the spectral domain and the time domain, each of which needs to be accounted for when specifying the performance of a TRPL system, in addition to the sensitivity and signal to noise. In the time domain, the most important parameter is the time resolution. For the electronic gating method which is based on fast response electronics, the time resolutions range from sub-nano to nanosecond. Two of the most widely use electronic gating methods are time-correlated single photon counting (TCSPC) [Y. V. Il'ichev, W. Kuhnle, and K. A. Zachariasse, J. Phys. Chem. A 102, 5670 (1998); M. P. Heitz and M. Maroncelli, J. Phys. Chem. A 101, 5852 (1997).] and streak cameras [Campillo, A., and S. Shapiro. *Quantum Electronics, IEEE Journal of* 19.4 (1983): 585-603; B. Gobets, I. H. M. Van Stokkum, M. Rogner, J. Kruip, E. Schlod-der, N. V. Karapetyan, P. Dekker, and R. Van Grondelle, Biophys. J. 81, 407 (2001).]. Although new generation streak cameras can have sub-picosecond time resolution, they suffer from low sensitivity and picosecond timing jitter causes difficulty in synchronizing the camera and the excitation laser. In the spectral domain, the most important parameter is the spectral bandwidth. The TCSPC is a single channel detection technique. This means that it needs several scans for different wavelengths to reconstruct the full time resolved spectrum. The streak camera can use a two dimensional detector as the sensor for broadband detection.

Although TRPL techniques with sub-nano to nanosecond time resolution have become standard tools in various fields, recent research interests have shifted to the ultrafast dynamics in sub-pico to picosecond time scale [Qiu, Weihong, et al. *Proceedings of the National Academy of Sciences* 104.13 (2007): 5366-5371; Messina, Fabrizio, et al *Nature communications* 4 (2013); Banerji, Natalie. *J. Mater. Chem.* C1.18 (2013): 3052-3066.]. The application of the ultrafast TRPL includes the ultrafast solvation dynamics [Jimenez, Ralph, et al. "Femtosecond solvation dynamics of water." *Nature* 369.6480 (1994): 471-473.], energy transfer [Klostermeier, Dagmar, and David P. Millar. *Biopolymers* 61.3 (2002): 159-179.] and charge transfer [Messina, Fabrizio, et al. *Nature communications* 4 (2013).] processes. Valuable information can be extracted from the spectra and the spectral evolution on the ultrafast time scale. Therefore, ultrafast broadband TRPL techniques are an important tool for both fundamental and applied research. Until now, it is still impossible to catch such short events with electronic gating methods. Modern ultrafast lasers and optical gate based on nonlinear optical process provide the solution for ultrashort time resolution. Femtosecond fluorescence up-conversion [Shah, Jagdeep, *Quantum Electronics, IEEE Journal of* 24.2 (1988): 276-288.] is the most widely used method for the optical gating TRPL. By using the fundamental output (800 nm) of the commercially available Ti-Sapphire laser system as the light source, the up-conversion system can perform with high sensitivity and sub-picosecond time resolution. However, the disadvantage of up-conversion TRPL is that the detection bandwidth is limited by the narrow phase matching bandwidth of the second order sum frequency process. Thus, it is difficult and time consuming to get the ultrafast spectra by the up-conversion system. It is possible to achieve broader phase matching for the up-conversion process by selecting special pumping wavelength nonlinear crystal and noncollinear phase matching [Zhang, X. X., C. Wurth, et al. (2011), Review of Scientific Instruments 82(6): 063108-063108.]. However, the design and implementation of the setup is complicated.

An alternative way to realize broadband ultrafast TRPL is the optical Kerr gate [Nakamura, R. and Y. Kanematsu (2004), 75(3): 636-644; Arzhantsev, S. and M. Maroncelli, 2005, *Appl. Spectrosc.* 59(2): 206-220.]. The ultrafast optical shutter is constructed by the Kerr medium and a pair of high quality polarizers and controlled by the optical Kerr effect induced by the ultrafast laser pulse. Theoretically, because of the inherent phase matching condition of the Kerr effect, the Kerr gate is an ideal design for the broadband ultrafast TRPL. Practically, its performance is limited by the useful bandwidth, and the transmission and extinction ratio of the polarizers. In the Kerr gate setup, because the un-gated PL and gated signal are collinear, a polarizer pair is needed with a high extinction ratio to block the un-gated PL. However, such polarizers are still unavailable, especially in the UV range, and the application of the Kerr gate system is limited to samples with short PL lifetimes and low quantum yields due to the difficulty in suppressing background PL.

Transient gratings (TGs) produced by the Kerr effect from laser pulses have been proposed for optical deflection schemes. See Alfano et al., U.S. Pat. No. 5,126,874 issued Jun. 30, 1992. Such optical deflection schemes have been limited by the relatively small amount of beam energy that is deflected compared to the incident or undeflected beam energy and compared to the beam energy required to create the transient grating. The dynamic TG response of a material can be used to study its photoexcitation dynamics [H J Eichler, P. Gunter, and DW Pohl, Laser-Induced Dynamic Gratings (Springer-Verlag, Berlin, 1986)]. Also, Lee et al. used a TG method to measure broadband ultrafast supercontinuum pulses [Lee, D., Gabolde, P., & Trebino, R. (2008), Journal of the Optical Society of America B, 25(6), A34].

DISCLOSURE OF THE INVENTION

The present disclosure provides a highly sensitive and background free ultrafast broadband method of time resolved luminescence measurement, such as time resolved photoluminescence (TRPL) spectroscopy and time resolved luminescence imaging. Such a technique is expected to be a powerful tool to study ultrafast electronic dynamics with broadband spectral resolution for strongly emissive samples, which cannot be done using any current existing technique. It can also provide a single detection technique able to capture broadband emission spectra covering from the sub-picosecond to nanosecond time scale.

The present disclosure uses a transient grating (TG) as an optical gating element for luminescence imaging or detecting broadband luminance spectra that may cover from the ultraviolet UV) to near infrared (NIR) with sub-picosecond time resolution. The luminescence image or broadband luminescence spectrum can be detected when it is several orders of magnitude lower in intensity than the laser pulse used to produce the transient grating. With a commercially available high power ultrafast laser system, sub-picosecond time resolution can be easily achieved. Compared with other existing broadband ultrafast TRPL techniques, for example, Kerr gating [Boyd, Robert W. *Nonlinear optics*, Academic press, 2003.], the use of a transient grating (TG) as the optical gating element provides a higher detection efficiency and without the need for expensive polarizers.

The present disclosure provides a polychromator system that can capture signals from the UV to IR without changing the optical setup in a short measurement time. The reconstruction of a time resolved spectrum is straightforward. With a commercially available high power ultrafast laser system, sub-picosecond time resolution can be achieved easily. The system has extremely low background noise in order to fulfil requirements for high sensitivity, background-free TRPL spectroscopy. The gating beam wavelength or the geometry of the system can be adjusted to change the detection bandwidth.

The present disclosure also provides an ultrafast imaging system capable of capturing images of light emitted from luminous material at spaced instants in time. The images can be resolved with sub-picosecond time resolution, and the spacing in time can be selected with sub-picosecond time resolution over a range up to one nanosecond or more. Thus, the ultrafast imaging system can not only resolve fine structure of the luminous material with sub-picosecond time resolution, but also determine the lifetimes of the fine structure with sub-picosecond time resolution over a wide range of picoseconds. The present disclosure also provides an ultrafast imaging system that records an image that is analogous to an image from a streak camera and without using any moving parts.

The polychromator or ultrafast imaging system may be formed with all reflective optics prior to the grating medium in order to minimize dispersion. In addition, the optics may have high numerical aperture optics to collect the light emitted from the luminous material and image this light to the gate medium with optimized numerical aperture. In addition, the light collecting optics may also be optimized to minimize stray light scattering.

For ultrafast time resolution and low background, the gate medium has a fast response time and large band gap. The gate medium should also have smooth surfaces in order to reduce background from undesired scattering of the gate beams and ungated PL. However, for applications that do not require ultrafast time resolution, slower gate material with higher nonlinearity can be used to detect slower dynamics. This would enable the use of a lower power gate beam and would achieve lower background noise for these applications.

MODES FOR CARRYING OUT THE INVENTION

Figure 1:
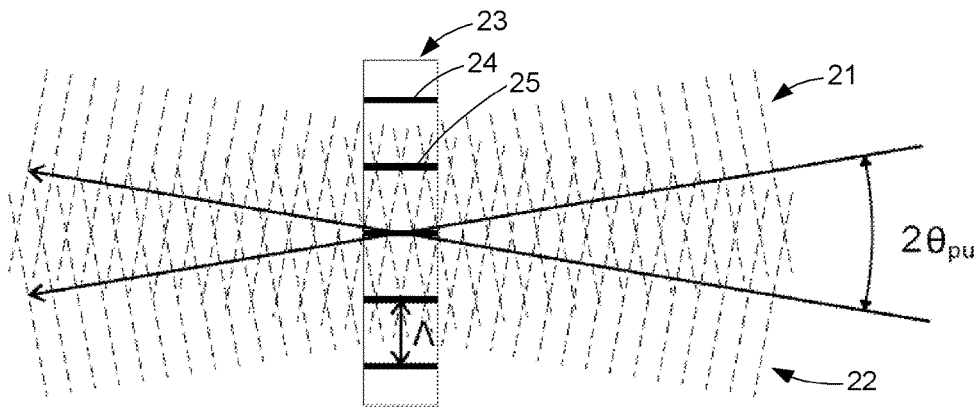
FIG. 1 shows two gate beams forming a transient grating (TG) in gate material.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale, certain parts have been omitted for clarity, and the proportions of certain parts have been exaggerated to better illustrate details and features of the present disclosure. For example, FIG. 3 shows details of components in a specific implementation of the system in FIG. 2, and similar components could be used in specific implementations of the systems of FIGS. 10, 11, and 12-13. For example, an adjustable optical delay line 60 is shown in FIG. 3 in order to balance the pathlengths of two gate beams 56, 57 that cross each other in the gate medium 59 in order to form a transient grating in the gate medium, and similar adjustable optical delays lines could be used for the same purpose in specific implementations of the systems of FIGS. 10, 11, and 12-13.

The disclosed embodiments involve time resolved luminescence measurement by imaging light emitted by a luminous material onto a photo-detector array. Because the light to be measured is emitted from rather than scattered by the luminous material, an optical shutter is interposed between the luminous material and the photo-detector array. For ultrafast time resolution, the optical shutter is a transient grating (TG) produced in a gate medium by one or more laser gate pulses. For time resolved luminescence spectroscopy, a polychromator is interposed between the luminous material and the photo-detector array.

For time resolved photoluminescence spectroscopy (TRPL), the laser gate pulse creates the TG a selected time after material absorbs light from a laser excitation pulse. For example, a pulse from a single laser is split into the excitation pulse and a gate pulse that travels thorough an adjustable delay line to the gate medium. A graph of the photoluminescence of the material as a function of time is built up from spectrum snapshots taken by the photo-detector array from a series of the laser pulses. For example, the photoluminescence of the material is used to identify the molecular makeup of the material.

The spectroscopy setup can also be used to measure Raman spectra. The setup is particularly advantageous for measuring strongly fluorescent samples under resonant excitation. Without time gating, long lived fluorescence would overwhelm the Raman scattering signal in the same wavelength region. Raman scattering can be separated from most of the PL background in the time domain, since scattering is instantaneous, while PL decays over a much longer timescale. In this application, the Raman pulse should have a narrow spectrum (and therefore a longer pulsewidth) to achieve sufficient spectral resolution. The TG pulses should be fixed to arrive at the grating medium at same time as the scattering. A Raman spectrum is obtained as the frequency shift between scattered peaks and the Raman pulse. The spectroscopy setup can also be extended to measure time-resolved Raman spectra of excited states via the addition of an actinic excitation pulse prior to the set of Raman and gate pulses.

For time resolved photoluminescence imaging, the photo-detector array may detect a two-dimensional image, and a polychromator need not be used. Otherwise, the system can be the same as the system used for TRPL. The two-dimensional image may show fine structure of luminous regions of the material. For example, the luminous regions may be trapping or defect sites in a semiconductor wafer or film. Different PL images of a semiconductor wafer or film over a range of time delays since the excitation pulses may provide measurement of the minority carrier lifetime in the neighborhood of the trapping or defect sites. Image data from the photo-detector array may be enhanced by deconvolution techniques, which may take into consideration the gate beam pulse shape and the gate medium response as a function of time. For improved spatial resolution, the excitation beam width can be increased to provide widefield illumination, and the collection optic can include a microscopic objective or reflective optics to achieve good spatial resolution of PL.

Time resolved luminescence imaging may also be done with a similar system in which two or more snapshot luminescence images of a luminescent material are taken at respective spaced instants in time. For example, a second snapshot is taken a selected time after a first snapshot, so that each snapshot image shows fine structure of luminescent regions of the of the material, and a comparison of the two snapshots images indicates the lifetimes of the luminescent regions. These measurements can be repeated and the repeated measurements can be combined to provide statistics of the size distribution and lifetimes of the various sizes of the fine structure. In this example, the same photo-detector array can be used to record the two snapshot images. For example, the gate pulse laser frequency or the geometry of the transient grating is changed between snapshots so that the transient grating diffracts the different snapshot images of the luminescent material to different respective regions of the photo-detector array.

Time resolved luminescence imaging may also be done with a similar system in which the photo-detector array records a streak image of a luminous object or its spectrum as a function of time. One way of doing this is to use a broadband chirped gate beam so that the deflection angle of a beam of light emitted by the sample and diffracted by the transient grating is a monotonic function of time so that the beam of light is swept across the photo-detector array. Another way of doing this by using a plate of gate medium as an image plate and forming a transient grating that is swept across the plate of gate medium.

By using a polychromator and a two-dimensional photo-detector array, the photo-detector array may detect a snapshot of spectra from respective spaced regions across the luminescent material. For example, the snapshot could indicate spectra of light emitted from regions across a semiconductor wafer or film, or across a plasma Z-pinch.

In a preferred implementation, the TG for the optical shutter is generated by a pair of gate laser pulses interacting in the gate medium. For example, as shown in FIG. 1, when two gate beam pulses 21 and 22 overlap spatially and temporally in a gate medium 23, they will generate an interference pattern, which is a periodic distribution of intensity with a characteristic grating shape shown in FIG. 1 as a series of heavy spaced parallel line segments 24, 25, etc.

The intensity distribution I(x) can be described by equation (i), $$I(x) = 2I_{pu}\left[1 + \cos\left(\frac{2\pi x}{\Lambda}\right)\right], \quad (i)$$

where $\Lambda$ is the fringe spacing, $$\Lambda = \lambda_{pu}/(2 \sin \theta_{pu}),\qquad\text{(ii)}$$

and $2\theta_{pu}$ is the crossing angle between two gate beams.

The interference fringe pattern can produce a TG in the gate medium by light-matter interaction. For example, a phase TG can result from the laser-induced refractive index change by optical Kerr effect. When the light emitted from a sample of luminous material interacts with the TG, a portion of the light from the sample will be diffracted and separated from an ungated portion the light from the sample. The diffraction angle $\phi$ will satisfy the Bragg condition $n\lambda_e = 2\Lambda \sin \phi$ where $\lambda_e$ is the wavelength of the light emitted from the sample, and $\phi$ is the angle between the light emitted from the sample and the plane of the TG. By selecting a gate medium with an ultrafast response time, the existence of laser induced TG can be as short as the time scale of the pulse width of the ultrafast laser. Thus, the TG can work as an ultrafast optical shutter because only the light emitted from the sample is diffracted to the photo-detector array on the ultrafast timescale of the gate pulse. By varying the delay time between an excitation laser pulse and the gate laser pulse, TRPL can be measured.

Figure 2:
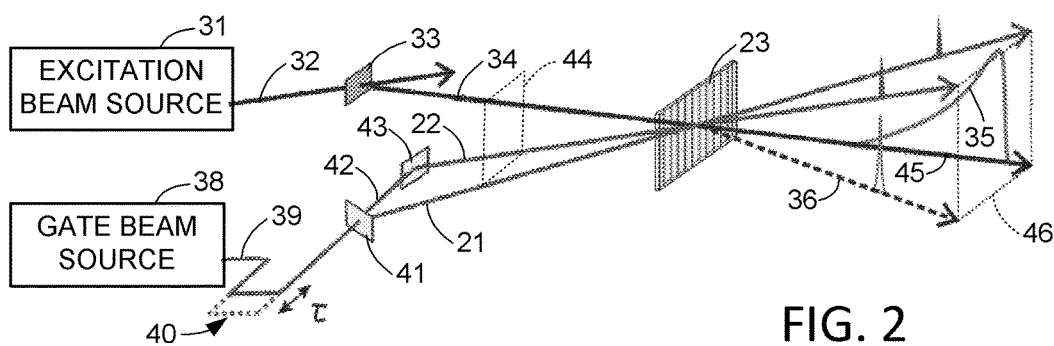
FIG. 2 is a schematic diagram of setup for using a transient grating as an optical shutter for time resolved photoluminescence (TRPL) imaging or spectroscopy.
Figure 3:
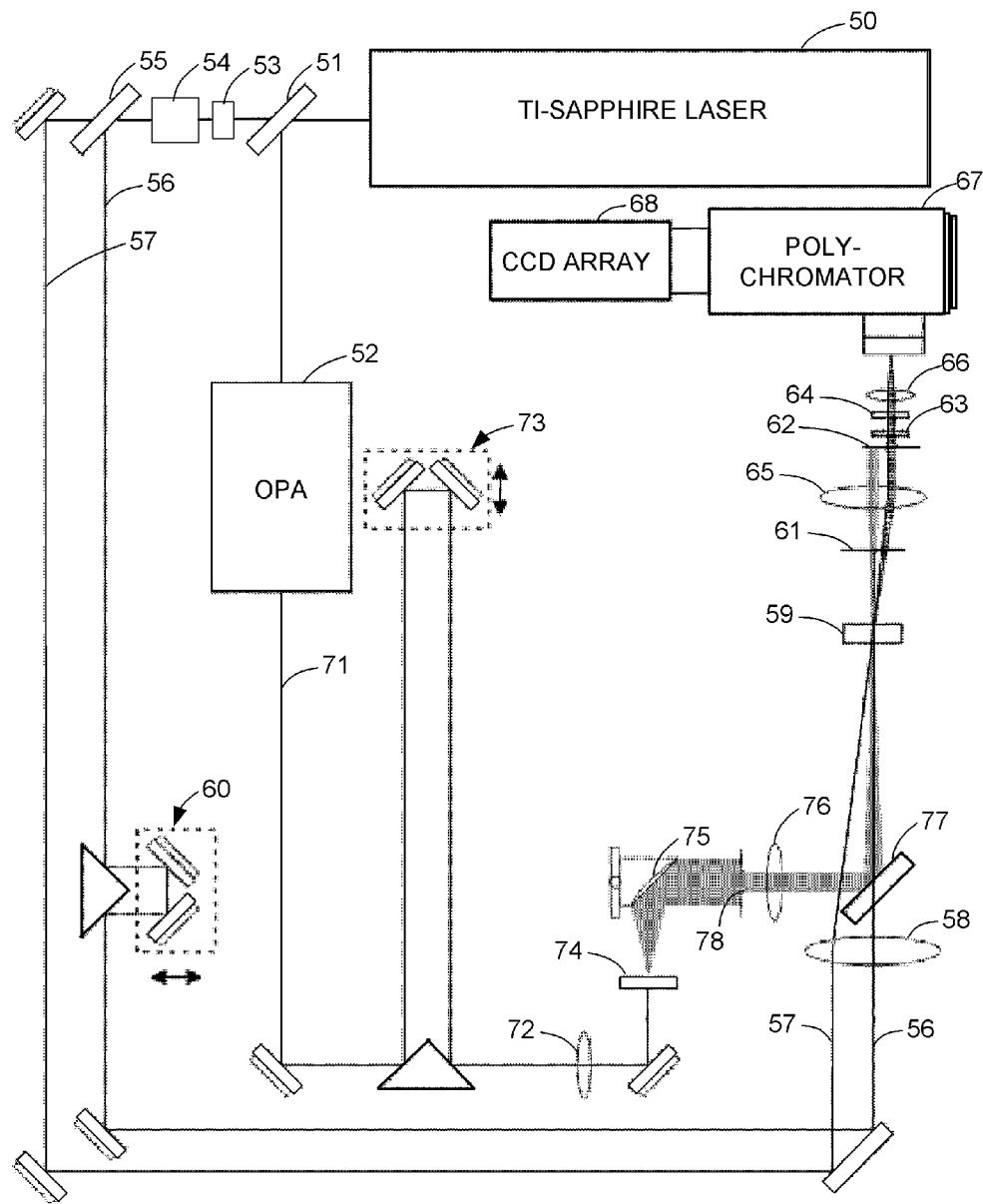
FIG. 3 is a more detailed schematic diagram of s setup for TRPL spectroscopy.

FIGS. 2 and 3 shows the basic setup of the TG for TRPL. An excitation beam source 31 directs a pulsed excitation beam 32 at a sample 33. The sample 33 is excited by absorption of photons from the pulse of the excitation beam, and subsequently the sample reverts to its unexcited state by emission of lower energy PL photons in directions different from the direction of the excitation beam. Some of these PL photons are directed as a beam 34 through the TG gate medium 23.

In the absence of a TG in the gate medium 23, the beam 34 passes through the gate medium 23 without deflection, and emerges from the gate medium 23 as a beam 45 having a broad pulse 35 with a fast rise time and an exponential decay. For the sake of illustration, the intensity of the pulse 35 is depicted as a deviation in the vertical direction from the direction of the beam 45, although it should be understood that the photons of the pulse 35 are generally confined in the direction of the Bragg condition.

As further shown in FIG. 2, gate beam source 38 produces a pulsed gate beam 39 synchronized with the pulsed excitation beam 32. The gate beam 39 is produced by an ultrafast pulse laser, for example, a Ti-sapphire regenerative amplifier.

In the preferred implementation of the TRPL system, the gate beam is delayed by a selected duration of time ($\tau$) in an adjustable optical delay line 40. This selected duration of time ($\tau$) determines the offset in time between the time that the sample 33 is illuminated by the pulse in the excitation beam 32 and the time that the TG is created in the gate medium 23. After the gate beam 39 passes through the optical delay line 40, it is split by a beam splitter 41 into two gate beams 21 and 42. These two gate beams 21 and 42 have about the same intensity. The gate beam 21 is aligned with the gate medium 23. The gate beam 42 is reflected by a mirror 43 to produce the gate beam 22, which is also aligned with the gate medium 23. The gate beams 21 and 22 interfere with each other in the gate medium 23 to produce the TG shown in FIG. 1. The TG deflects a portion of the PL beam 34 to produce the gated PL beam 36. The gated PL beam 36 is also pulsed, but the duration and timing of the gated PL pulse is synchronized with the pulses of the gate beams 21 and 22. As will be further described below with respect to FIG. 3, the gated PL beam 36 is directed to a photo-detector array, and for TRPL spectroscopy, a polychromator is interposed between the gate medium 23 and the photo-detector array.

The TG efficiency can be estimated by the equation based on the low diffraction limit of volume phase grating: $\eta = (\pi n_1 d/\lambda \cos \theta)^2$ [Kogelnik, Herwig, The Bell System Technical Journal, Vol. 48, no. 9, November 1969, pp. 2909-2947.], where $n_1$ is the refractive index modulation depth, d is the grating thickness, and $\lambda$ and $\theta$ are the incident wavelength and angle of gate beams, respectively.

When the TG exists in the gate medium 23, the amplitude of the gated PL pulse 36 is proportional to the amplitude of the PL pulse 35, so that the gated PL pulse is a snapshot of the PL pulse 35. The gated PL pulse has some delay with respect to rise time and the fall time of the pulses of the gate beams 21, and this delay depends on the response time of the gate medium. For a gate medium of UV-fused silica, the response time is not significant in comparison to the pulse width of the gate beams 21 and 22 and the gated PL beam 36.

The detection bandwidth of the TG TRPL depends on the phase matching condition which relates to the optical setup geometry, acceptance of the gate beams 21, 22, and the crossing angle of the gate beams. Broader detection bandwidth can be achieved by increasing the acceptance angle and decreasing the crossing angle of the gate beams. It is also possible to change the optical geometry for a desirable wavelength region.

In a preferred implementation, as shown in FIG. 2, the geometry of the TG TRPL is a BOXCAR arrangement [Eckbreth, Alan C. Applied Physics Letters 32 (1978): 421.]. The advantage of the BOXCAR geometry is the gated signal 36 can be easily separated from the ungated light 35 emitted from the sample and the intense gate beams 21, 22. For example, the two collimated and parallel gate beams are focused by a lens and correspond to the beams 21, 22 at corners of a rectangular 44 in an input plane. The light emitted from the sample is collected and focused on the TG from another corner of the rectangle 44. After the gate medium, the ungated PL 45 and two gate beams 21, 22 map to the three corners of a rectangle 46 in the output plane, and the gated PL 36 diffracts to the fourth corner.

In order to achieve ultrafast time resolution and avoid background from the multiple photon excitation in the gate medium, UV-fused silica is used as the gate medium. It is also possible to use other gate media having higher nonlinearity for different requirements. Such other gate media include strontium titanate, yttrium aluminium garnet, gadolinium gallium garnet, benzene, and toluene. Such other gate media may reduce the energy requirement of the gate beam and reduce the background at the expense of reduced time resolution.

To satisfy the broadband phase matching condition, the gate beams are focused with a wide acceptance angle in the horizontal plane (formed by the vector of the transient grating and wave vectors of the gate beams). The gate beams can be shaped by cylindrical lenses with shorter focal length in the horizontal plane and long focal length in the vertical plane to increase the phase matching bandwidth and avoid self-focusing due to high order process.

In order to achieve broadband detection, one of the most important properties of the TG system is the phase matching bandwidth. For the case of degenerate TG, in which the wavelength of the gate beam and light emitted from the sample are the same, the phase matching condition is satisfied automatically for all wavelengths and geometries. In the more practical case of non-degenerate TG, the wavelength of the light from the sample is different from the gate beam. Non-degenerate TG is more practical because the difference in wavelength between the light from the sample and the light from the gate beam permits a filter or polychromator interposed between the TG and the detector array to remove or separate background from the gate beam from light emitted from the sample. However, the broadband phase matching condition can still be satisfied for the case of non-degenerate TG by suitable selection of various system parameters related to the gate beams and the geometry of the TG.

The broadband phase matching condition is a function of the bandwidth of the gate beams. Since a femtosecond laser pulse has a wide bandwidth inversely proportional to the pulse width, it provides extra k-vectors to increase the phase matching bandwidth.

The broadband phase matching condition is a function of the bandwidth of the k-vectors of the gate beams. In order to produce enough intensity to induce the Kerr effect, the gate beams are focused on the gate material. Therefore the k-vectors of the incident beam cover a range of angles and have more bandwidth than they would if they would not cover a range of angles.

The broadband phase matching condition is a function of the size of the TG. Because of the finite size of the TG, the k-vector spectrum can be described by the equation:

$$G(\vec{K}) = \left[\delta(\vec{K}) + \frac{1}{2}\delta(\vec{K} - \vec{K_g}) + \frac{1}{2}\delta(\vec{K} + \vec{K_g})\right] \otimes XYZ \quad \text{(iii)}$$
$$\operatorname{sinc}\frac{Xk_X}{2\pi}\operatorname{sinc}\frac{Yk_Y}{2\pi}\operatorname{sinc}\frac{Zk_Z}{2\pi}.$$

For an infinite grating, the k-vector for the first order diffraction is only with single value (dirac-delta function) thus only a single wavelength can be diffracted. However, the convolution is from the effect of the finite size of the grating. The convolution blurs the delta function and supports more k-vectors for the broadband diffraction [Goodman, Joseph W. *Introduction to Fourier optics*, Roberts and Company Publishers, 2005.].

The broadband phase matching condition is a function of the crossing angle between the two gate beams. According to the coupled mode theory [Kogelnik, Herwig, "Coupled wave theory for thick hologram gratings," *The Bell System Technical Journal, Vol.* 48, no. 9, November 1969, pp. 2909-2947. Vol. 48, 1969.], the wavelength mismatch of the diffractive efficiency is proportional to $$\frac{\Delta\lambda}{2\Lambda}$$

where Λ is the period of the transient grating. Thus, broader phase matching bandwidth can be achieved by smaller crossing angle of the gate beams.

Overall, although the phase matching bandwidth of the TG is not satisfied for all wavelengths as it is for Kerr gating, broadband phase matching can be easily achieved by increasing the numerical aperture of the gate beams and reducing the crossing angle between the gate beams. For example, by considering the available k-vectors of the gate beams, Lee et al demonstrated a FROG setup for characterizing white-light supercontinuum pulses with phase matching bandwidth from 380 to 1600 nm by a 800 nm gate beam [Lee, D., Gabolde, P., & Trebino, R. (2008), Journal of the Optical Society of America B, 25(6), A34]. The phase-matched bandwidth can be calculated based on the range of signal k-vectors generated for a given geometry using the equation $k_S^{\rightarrow}\pm/k_S^{\rightarrow}=\sin(\theta/2)/\sin((\theta\mp\phi)/2)$, where $k_S^{\rightarrow}\pm$ are the k-vectors matched to the blue and red spectral edges of the signal, $k_S^{\rightarrow}$ is the degenerate k-vector, θ is the gate beam crossing angle, and φ is the focussing cone angle of the gate beams. Applying this analysis to the configuration detailed and demonstrated here, the phase-matched bandwidth therefore spans 340 to 1300 nm.

In the following working example of FIGS. 3, 4 and 5, the bandwidth was limited by the optics and the detector array rather than the phase matching bandwidth of the TG. The bandwidth was sufficient to measure ultrafast TRPL dynamics for a real emissive sample with a range of properties.

It is also possible to expand broadband detection further into the UV and near-IR simply by adjusting the focusing geometry or decreasing the thickness of the grating medium. Unlike broadband upconversion and downconversion, the choices of nonlinear medium and gate wavelength are essentially decoupled from the focusing geometry, thus eliminating the need to revisit the nonlinear crystal type, thickness and cutting angle and the gate wavelength when moving to a new spectral window.

FIG. 3 shows the layout of the TG TRPL system. The light source of the TG TRPL system was a Ti-sapphire femtosecond laser/amplifier 50. The output laser pulse was at 800 nm. The pulse duration was 100 fs, and the repetition rate was set at 3 kHz. A beam splitter 51 split the output into a first part (0.3 mJ/pulse) for producing the excitation beam and a second part (40 uJ/pulse) for producing the gate beams. The first part was fed to an optical parametric amplifier (OPA) 52. The OPA was a model TOPAS-C from Light Conversion Ltd of Vilnius, Lithuania, EU. The OPA was tunable to provide an excitation beam at a selected frequency different from the frequency of the Ti-sapphire laser 50. In an alternative arrangement, the OPA could be replaced with a harmonic generator to produce an excitation beam at a multiple of the frequency of the Ti-sapphire laser 50.

The second part from the beam splitter 51 was shaped by cylindrical lenses 53 to a shape with a width of ~8 mm and a height of ~2 mm, and then raised 25 mm vertically by a periscope 54 and further separated into two gate beams 56, 57 with equal intensity by a 50-50 beam splitter 55. The two gate beams 56, 57 were directed by a series of mirrors and focused by a lens 58 with focal length 150 mm onto the gate material 59 with a cross angle of 5 degrees to form the interference fringe pattern and induce the TG. The optical path of the two gate beams was fine tuned for timing overlap of the two gate pulses by an adjustable optical delay 60 on the gate beam 56. This timing overlap could be checked by replacing the gate material with a nonlinear crystal for second harmonic generation and autocorrelation.

A structure on an aperture 61 blocked the gate beams 21, 22 issuing from the gate medium 23. An aperture 62 was used to spatially filter out the ungated background PL and let through only the gated PL. A long-pass filter 63 blocked scattering of the excitation pulse, and a short pass filter 64 blocked scattering of the gate beams 56, 57 from the gate medium 59. Lenses 65 and 66 collected and delivered the gated signal to a polychromator 67 to produce a spectrum, and the spectrum was measured by a CCD photo-detector array 68. The polychromator 67 was a Model SP 2300 spectrometer from Princeton Instruments of Trenton, N.J., and the CCD photo-detector array was a PIMAX3 intensified CCD camera from Princeton Instruments. A non-intensified CCD, an EM-CCD, or a CMOS photo-detector array could have been substituted for the intensified CCD photo-detector array 65. The system operation and data acquisition was controlled by a LabVIEW program.

The OPA 52 generated a wavelength tunable excitation beam 71. The excitation beam 71 was directed by a series of mirrors to a lens 72. This optical path of the excitation beam 71 was controlled by a motorized delay line 73. The lens 72 focused the excitation pulse upon a sample 74 by the lens 72. The emission of the sample 74 was collected by a silver off-axis parabolic mirror 75 (1 inch diameter and 1 inch effective focal length) and then focused on the gate medium 59 (1 mm thick wafer of fused silica) by an achromatic lens 76 with 20 cm focal length, and a mirror 77. An aperture 78 was used to control the beam size of the fluorescence emission. The residual of the excitation laser beam was also blocked by a structure on the aperture 78.

The time overlap between the two gate beams 56, 57 was adjusted by the delay line 60. When the two gate beams overlapped in time and space, the intensity distribution induced a transient grating on the gate medium 59 by the Kerr effect. Once the sample fluorescence (which was excited by the excitation pulse) interacted with the transient grating, the gated signal was diffracted to the direction satisfying the Bragg condition. The arriving time to the gate medium between the sample florescence and the gate beams was controlled by the delay line 73. Because of the BOX-CAR geometry, the gate beams and un-gated fluorescence were spatially blocked by two apertures 61 and 62 respectively.

With this setup, the TG-TRPL system achieves >5% gate efficiency at 500 nm, ~200 fs time resolution, and enough detection bandwidth to cover the entire visible region from 400 to 720 nm, with a calculated bandwidth spanning 340 to 1300 nm.

Figure 4:
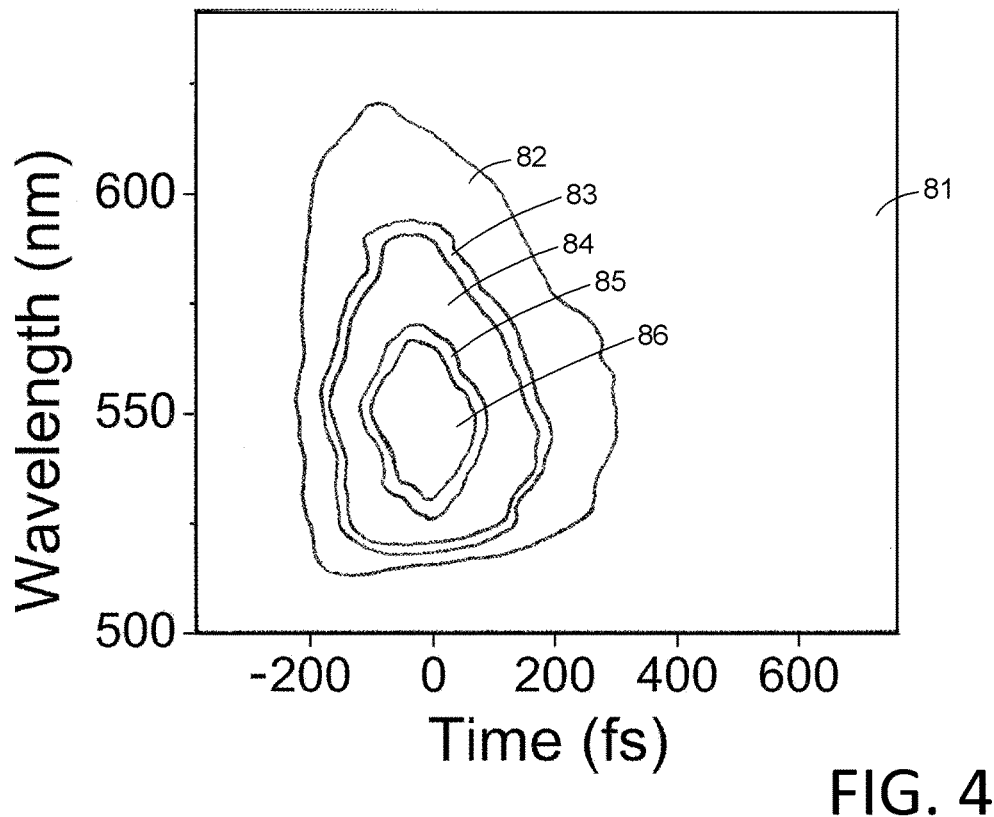
FIG. 4 shows TG TRPL dynamics for beta carotene in toluene as captured by the setup in FIG. 3.

FIG. 4 shows TG TRPL dynamics for beta carotene in toluene as built up from data from the CCD camera in the system of FIG. 3 for a series of laser pulses. In this case the TG TRPL dynamics followed 100 fs of photoexcitation at 480 nm with an excitation energy of 10 nJ/pulse for each laser pulse. Spectra from multiple pulses for one adjustment of the delay line were captured and averaged to produce the spectrum for a given time delay since photoexcitation.

FIG. 4 is a two-dimensional representation of a function of two independent variables, which are wavelength and time. This two-dimensional representation has different regions of different respective levels of normalized PL. In practice, the different regions are color-coded in the same way that a topographical map is color-coded to show elevation. The colors range from violet representing a zero or background level, to red representing a maximum level of one. In FIG. 4 the regions include a region 81 that would be colored violet, a region 82 that would be colored blue, a region 83 that would be colored green, a region 84 that would be colored yellow, a region 85 that would be colored orange, and a region 86 that would be colored red.

Figure 5:
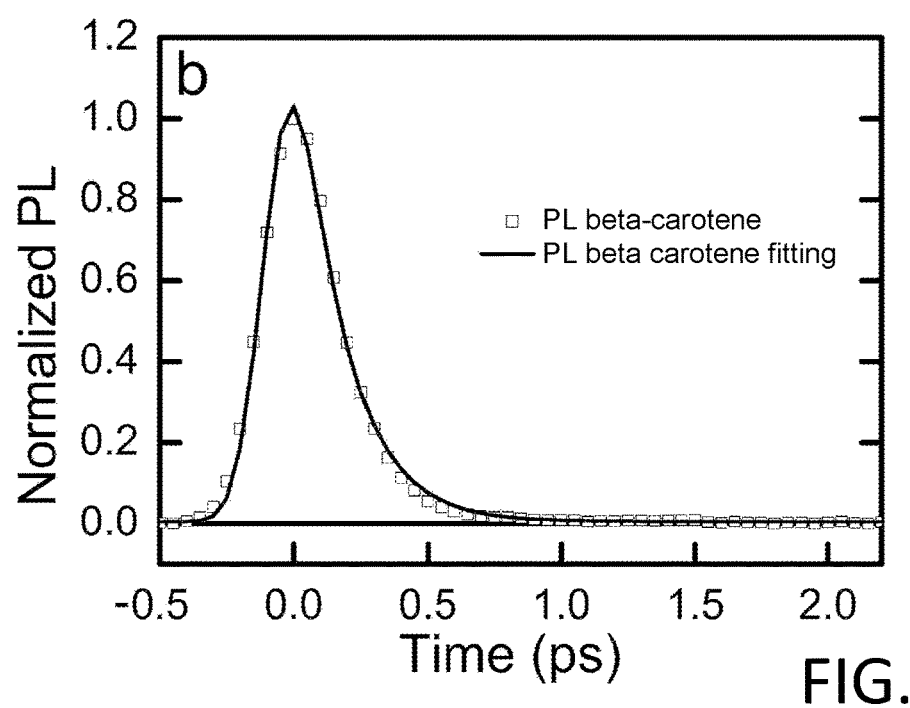
FIG. 5 shows kinetics extracted from the data set of FIG. 4.

FIG. 5 shows kinetics extracted from the data set used to build up FIG. 4, demonstrating the utility of the TG TRPL system for measuring ultrafast broadband dynamics.

Figure 6:
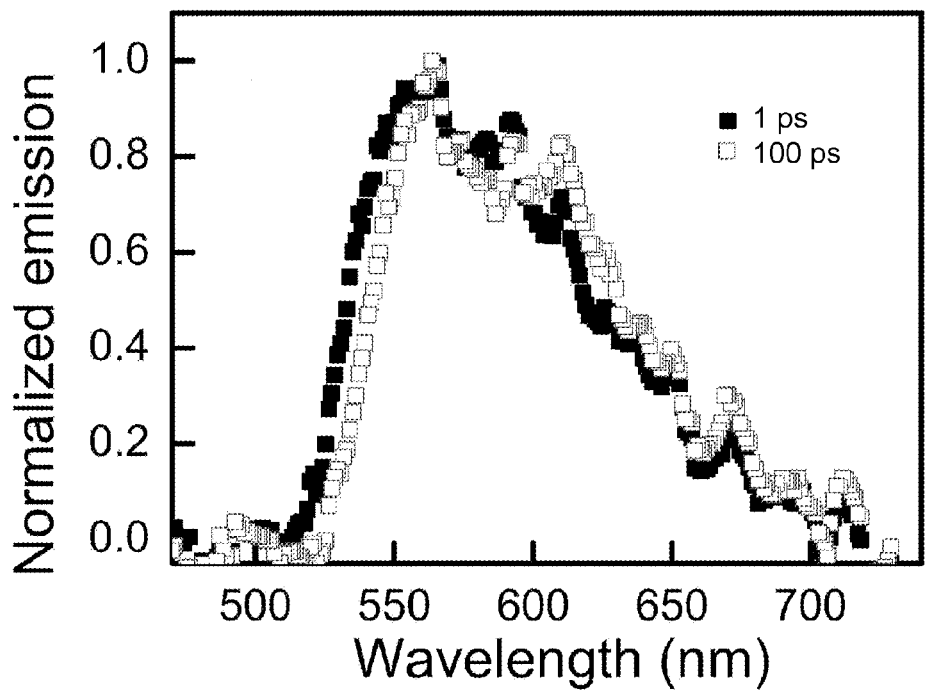
FIG. 6 shows TG TRPL dynamics for an oligothiopene in chloroform as captured by the setup in FIG. 3.

FIG. 6 shows TG TRPL dynamics for an oligothiophene in chloroform as built up from data from the CCD camera in the system of FIG. 3 for a series of laser pulses. In this case the TG TRPL dynamics followed 100 fs photoexcitation at 480 nm, with an excitation pulse energy of 2 nJ/pulse for each laser pulse. Spectra at 1 ps and at 100 ps after the excitation are shown in FIG. 6. For each delay, spectra from multiple pulses for one adjustment of the delay line were captured and averaged.

Figure 7:
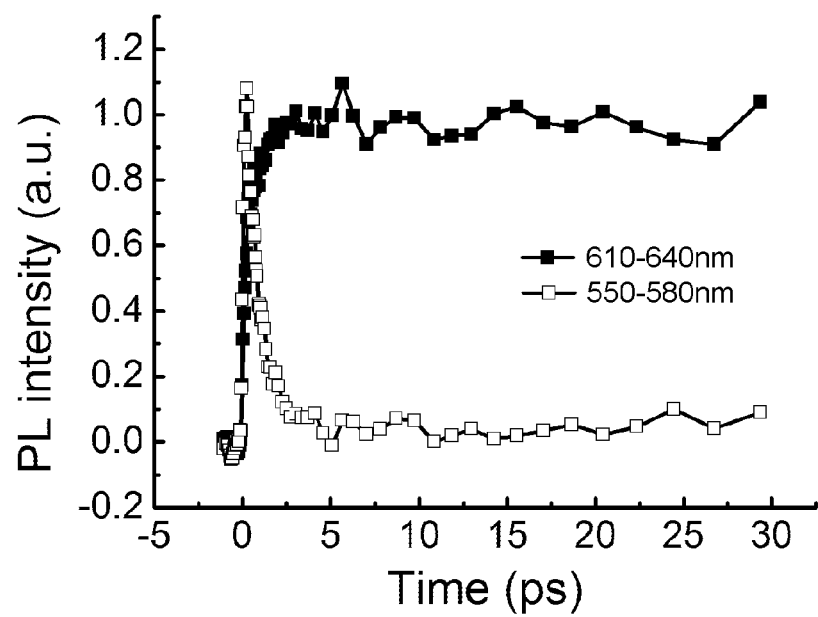
FIG. 7 shows TG TRPL kinetic traces of two spectral windows for a perylene-based multichromophore array.

FIG. 7 shows TG TRPL kinetic traces of two spectral windows for a perylene-based multichromophore array. The multichromophore arrays are covalently linked donor and acceptor perylene derivatives. The wavelength region of 550-580 nm correlates to the PL emission of the donor moieties, and the wavelength region of 610-640 nm correlates to the PL emission of the acceptor moieties. FIG. 7 shows the TG TRPL system can simultaneously resolve PL kinetics with short (sub-picosecond) and long (nano-second) PL kinetics.

Figure 8:
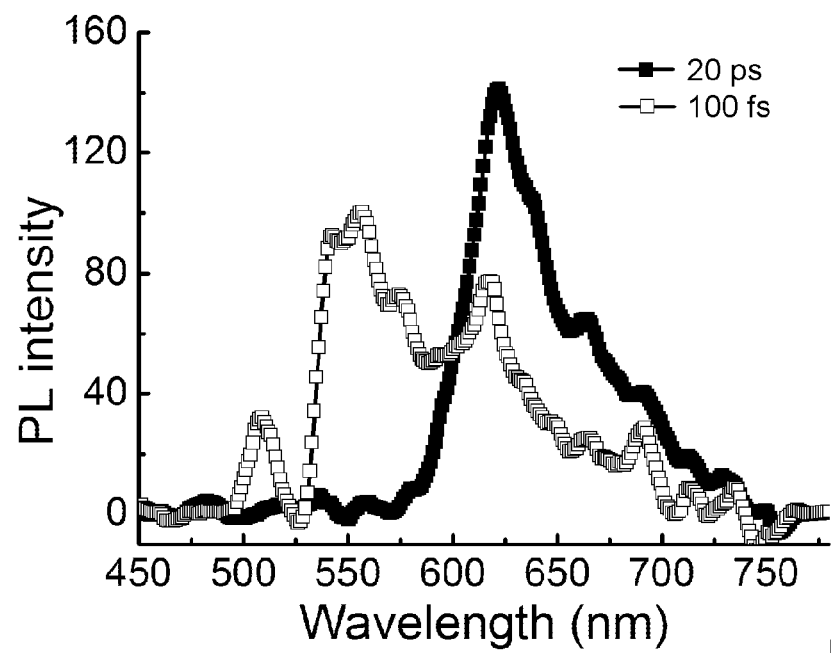
FIG. 8 shows time resolved PL spectra for a perylene-based multichromophore array at various time delays after 500 nm excitation.

FIG. 8 shows time resolved PL spectra for a perylene-based multichromophore array at various time delays after photoexcitation. The excitation source is 100 fs laser pulse at 500 nm and the pulse energy is 2 nJ/pulse. Spectra at 100 fs and at 20 ps after the excitation are shown in FIG. 8.

Figure 9:
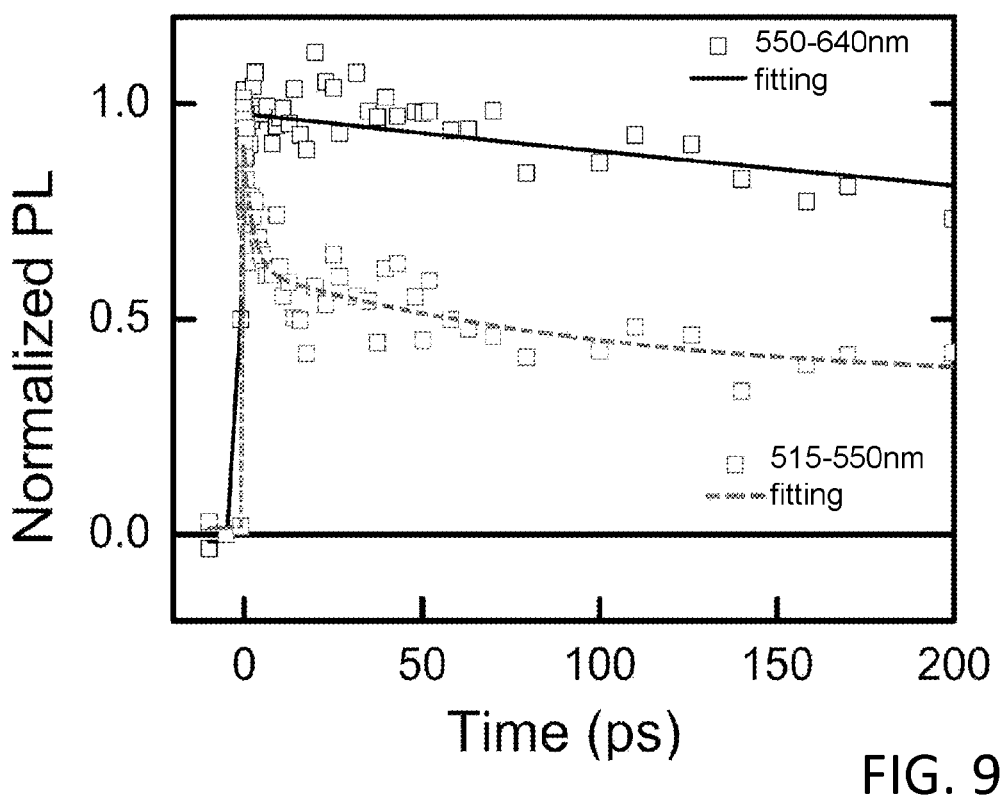
FIG. 9 shows kinetics extracted from the dataset of FIG. 6.

FIG. 9 shows integrated wavelength kinetics of 550-640 nm and 515-550 extracted from the dataset used to build up FIG. 6, demonstrating that the TG TRPL system maintains its utility even in probing long-lived highly emissive photoexcitations.

Figure 10:
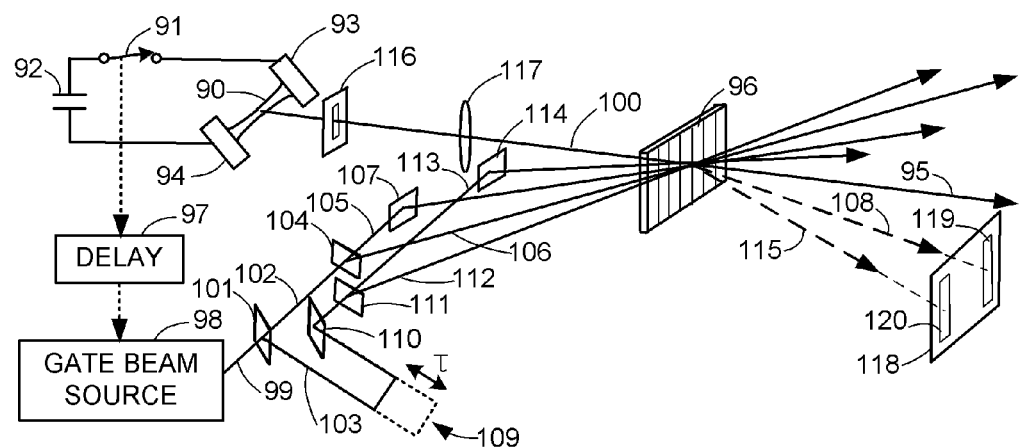
FIG. 10 shows a modification of the setup in FIG. 2 in order to capture two TG luminescence images spaced in time by a selected duration of time.

FIG. 10 shows a modification of the setup in FIG. 2 in order to capture two TG luminescence images 119, 120 spaced in time by a selected duration of time ($\tau$). In FIG. 10, the luminescent source is a plasma Z-pinch 90 formed by closing a switch 91 to discharge current from a capacitor 92 across a pair of spaced electrodes 93, 94. Light emitted by the source is formed into a beam 110 by a mask 116 and a lens 117, and most all of this beam 100 passes through the TG gate medium 96 and issues from the TG gate as an undeflected beam 95 until a TG is formed in the gate medium 96.

To form TGs in the gate medium 96, a gate beam source laser 98 is triggered to emit a pulsed beam 99 a certain delay 97 after the switch 91 closes. A first 50-50 beam splitter 101 splits this pulsed gate beam 99 into two a first part 102 and a second part 103. The first part 102 passes through the beam splitter 101 to a second 50-50 beam splitter 104. The second beam splitter 104 splits the first part 102 into a first gate beam 105 and a second gate beam 106. The first gate beam 105 is deflected by a mirror 107 to the gate medium 96. The second gate beam 106 passes from the second beam splitter 104 directly to the gate medium 96. In the gate medium 96, the first gate beam 105 interferes with the second gate beam 106 to form a first TG that diffracts a portion of the source beam 100 to form a first gated and deflected source beam 108. The first gated and deflected source beam 108 is directed to a two-dimensional photo-detector array 118 in order to form a first image 119 on the photo-detector array 118.

The second part 103 from the first beam splitter 101 passes through an optical delay line 109, which is adjusted to provide the selected duration of time ($\tau$). A mirror 110 directs the second part 103 from the delay line 109 to a third 50-50 beam splitter 111. The third beam splitter 111 splits the second part 103 into a third gate beam 113 and a fourth gate beam 112. The third gate beam 113 is deflected by a mirror 114 to the gate medium 96. The fourth gate beam 112 passes from the third beam splitter 111 directly to the gate medium 96. In the gate medium 96, the third gate beam 113 interferes with the fourth gate beam 112 to form a second TG that deflects a portion of the source beam 100 beam to form a second gated and deflected source beam 115. The second gated and deflected source beam 115 is directed to the two-dimensional photo-detector array 118 in order to form a second image 120 on the photo-detector array 118.

Because the crossing angle of the third and fourth gate beams 112, 113 in the gate medium 96 is greater than the crossing angle of the first and second gate beams 105, 106, the second gated and deflected source beam 115 is deflected by a greater angle than the first gated and deflected source beam 108. Consequently, the first and second gated and deflected source beams 108, 115 are directed to different respective locations on the photo-detector array 118. Also due to the mask 116, the first and second deflected source beams 108, 115 form respective non-overlapping images 119, 120 on different and non-overlapping regions of the photo-detector array 118. Consequently, the second image 120 is formed from light emitted from the same region across the source 90 as the first image 119 but at a later time, and the difference in time between the first image 119 and the second image 120 is the selected delay ($\tau$). Therefore the second image 120 can be compared to the first image 119 to determine lifetimes of fine structure appearing in the first image 120. This measurement process can be repeated many times and the results be combined to gather statistics about the size, geometry, and lifetimes of the fine structure despite the fact that positions of the fine structure in the images 119, 120 may change randomly between successive discharges of the capacitor 92 and corresponding shots of the gate beam source 98.

Figure 11:
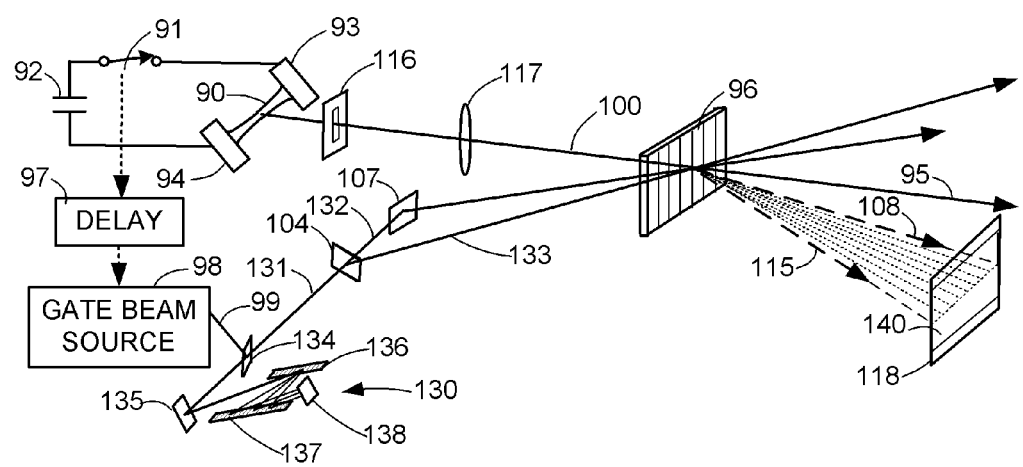
FIG. 11 shows a modification of the setup in FIG. 10 in order to produce a streak image of a luminous source by using a chirped gate beam.

FIG. 11 shows a modification of the setup in FIG. 10 in order to produce a streak image of the luminous source 90 or its spectrum by using a chirped gate beam 131. In this case the ultrafast pulse from the pulsed bate beam 99 is stretched out in time by a dispersive pulse stretcher 130 to produce the chirped gate beam 131. In this example, the stretched out pulse has its highest frequency at the beginning of the stretched-out pulse, and its lowest frequency at the end of the stretched-out pulse. For example, the dispersive pulse stretcher includes a beam splitter 134, a mirror 135, two diffraction gratings 136, 137, and a mirror 138.

The chirped gate beam 131 is split by the beam splitter 104 into a pair of chirped gate beams 132, 133 that cross each other in the gate medium 96 to produce a transient grating in the gate medium. Because the gate beams 132, 133 are chirped, the fringe spacing $\Lambda$ of the transient grating changes with time from a short fringe spacing to a long fringe spacing. Consequently, the changing transient grating deflects the light beam 100 emitted from the source 90 initially with a maximum deflection angle to produce an initial deflected beam 115 and finally with a minimum deflection angle to produce a final deflected beam 108 with a minimum deflection angle. Consequently, the deflected beam is swept across the photo-detector array 118 (in a direction from left to right in FIG. 11) so that the photo-detector array 118 records a streak image of the light emitted by the source 90.

In the setup of FIG. 11, the mask 116 selects an image in the form of a strip in a transverse direction (vertical in FIG. 10) across the source 90 so that the streak image on the photo-detector array records how this strip image changes over the duration of time of the chirped gate pulses 132, 133. In an alternative arrangement, a polychromator could be disposed between the source 90 and the photo-detector array 119, so that the streak image on the photo-detector array would record how the spectrum from the source 90 would change over the duration of time of the chirped gate pulses 132, 133. For example, the polychromator would be oriented to disperse the light emitted by the source in a direction perpendicular to the sweeping of the deflected beam 115, 108 (vertical in FIG. 10), and the polychromator could be disposed between the source 90 and the gate medium 96 or between the gate medium 96 and the photo-detector array.

The technique of using a chirped gate beam to sweep the deflected light emitted by the source across the photo-detector array has the capability of providing a sweep rate that can be selected over a very wide range because it is practical to stretch out an ultrafast laser pulse by orders of magnitude in time. For sweeping at even slower rates, the gate pulse could be provided by a tunable optical parametric amplifier. However, for very fast sweeping, an alternative method of sweeping a transient grating across a plate of gate medium provides a sweep camera that does not require a chirped gate pulse. This alternative method is based on the TG sweeping technique of FIG. 3 of Lee, D., Gabolde, P., & Trebino, R. (2008), Journal of the Optical Society of America B, 25(6), A34.

Figure 12:
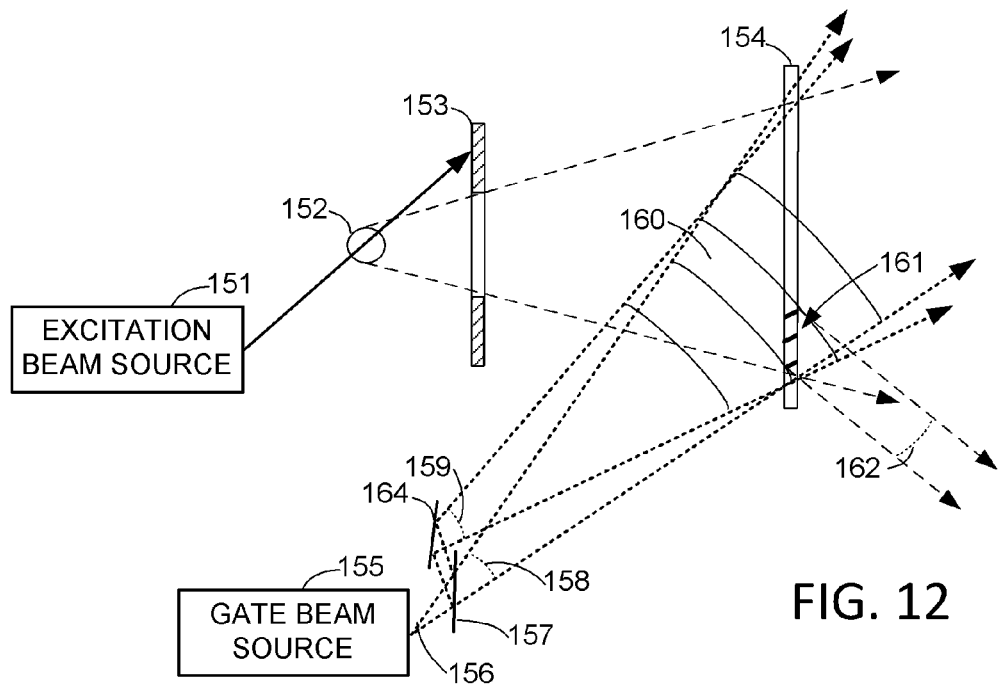
FIG. 12 shows a modification of the setup in FIG. 2 in order to produce a streak image of a luminous source or its spectrum by using a plate of gate medium as an image plate and streaking a transient grating across the plate of gate medium.

As shown in FIG. 12, a transient grating 161 is created in a plate 154 of gate medium by the intersection of the plate 154 with a region 160 of crossing of two gate pulses of two crossed gate beams 158 and 159. In contrast to the configurations discussed above, the transient grating 161 has a size that is a small fraction of the size of the plate 154 of gate medium. The crossing angle between the two gate beams 148 and 159 can be the same as it was for the other configurations discussed above, but in FIG. 12 there is a distribution of arrival times of the gate pulses from the bottom to the top of the grating medium defined by the pulse wavefronts (which is a function of the crossing angle between gate and signal beams). Consequently, over this distribution of arrival times, the transient grating 161 moves across the plate 154 of gate medium from the initial configuration shown in FIG. 12 to a final configuration in FIG. 13. Also, the crossing angle between the light emitted by the source 152 and the gate beams 158, 159 has been increased. As before, light emitted by the source illuminates substantially all of the gate medium, but at any given time, the TG deflects the source illumination as a beam 163 from only a small portion of the plate 154 of gate medium.

Figure 13:
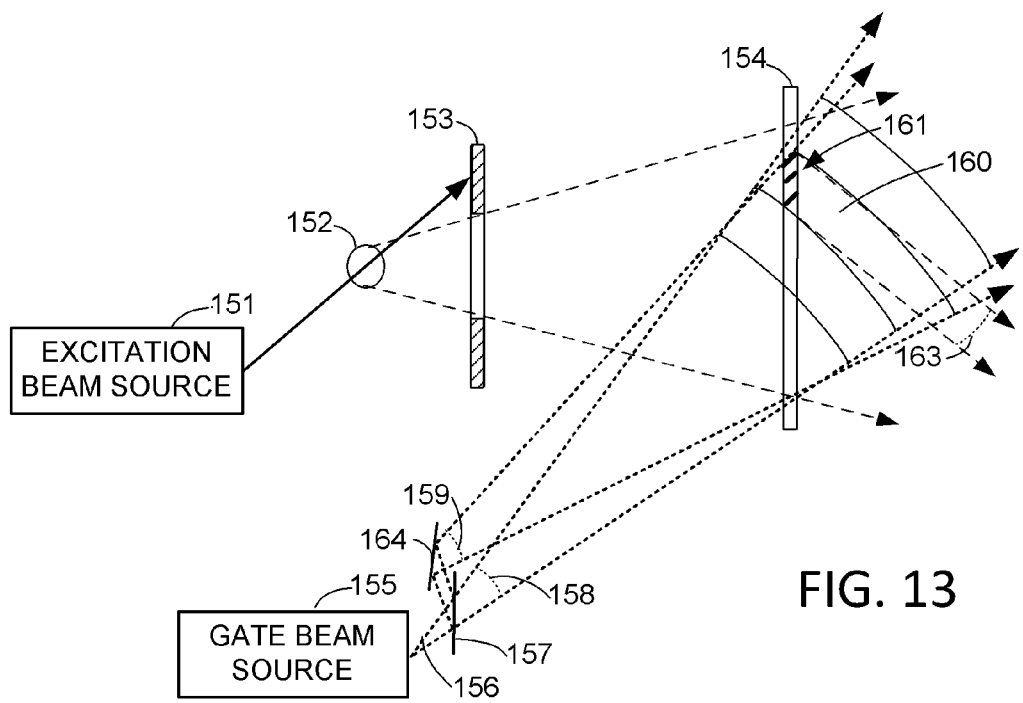
FIG. 13 shows the setup of FIG. 12 at the end of the sweep of the transient grating across the plate of the gate medium. The gate beams in FIG. 12 and FIG. 13 are depicted as divergent only to exaggerate the spatio-temporal variation of the transient grating.

In the configuration of FIGS. 12 and 13, the plate 154 functions as an image plate. The deflected beam 162 is directed to a photo-detector array for TG luminescence imaging or to a polychromator and photo-detector array for TRPL spectrometry as before, but the image on the plate of the gate medium (rather than the image of the luminous source) is focused upon the photo-detector array.

FIGS. 12 and 13 show the setup of a source 152 for TRPL imaging or spectrometry. An excitation beam source 151 excites the PL source 152, and light emitted by the PL source passes through a mask 153 to illuminate substantially all of the plate 154 of gate medium. A gate beam source 155 produces a gate beam 156, and a 50-50 beam splitter 157 splits the gate beam 156 to produce the gate beam 158 and the gate beam 159, and a mirror 164 directs the gate beam 159 to the plate 154 of gate medium. For example, as before, the gate beam source 156 is an ultrafast pulsed laser, and the excitation beam source 151 is a tunable optical parametric amplifier excited by the gate beam source 156.

The setup of FIGS. 12 and 12 could be modified for streak imaging of a luminous source such as a Z pinch by focusing an image of a transverse strip across the Z pinch onto the plate 154 with lenses, including a cylindrical lens that would expand the image of this strip across the plate 154 from bottom to top. The source configuration would be similar to the configuration of FIGS. 10 and 11 but the additional cylindrical lens would be inserted between the aperture 116 in FIG. 10 and the gate medium (96 in FIG. 10), corresponding to 154 in FIG. 12. The axis of the cylindrical lens would be parallel to the slit of the aperture and perpendicular to the Z axis of the Z pinch.

Numerous examples are provided herein to enhance understanding of the present disclosure. A specific set of examples are provided as follows.

In a first example, there is disclosed a method of measuring light emitted by a source, said method comprising: (a) imaging light from the source onto a photo-detector array at a selected instant in time by disposing a gate medium between the source and the photo-detector array and also illuminating the gate medium with at least one pulsed gate beam to form a transient grating in the gate medium at the selected instant in time; and (b) collecting measurements from the photo-detector array of the light imaged onto the photo-detector array.

In a second example, there is disclosed a method according to the preceding first example, wherein said at least one pulsed gate beam is produced by a femtosecond pulsed laser and the transient grating persists in the gate medium for less than one picosecond so that the measurements collected from the photo-detector array resolve the light imaged from the source with sub-picosecond time resolution.

In a third example, there is disclosed a method according to any of the preceding examples, wherein the pulsed gate beam is chirped to sweep the imaged light from the source across the photo-detector array.

In a fourth example, there is disclosed a method according to any of the preceding examples, wherein the gate medium is configured as an image plate, and the transient grating occupies a fraction of the image plate and sweeps across the image plate.

In a fifth example, there is disclosed a method according to any of the preceding examples, which includes illuminating the gate medium with two pulsed gate beams crossing each other in the gate medium to form an interference pattern in the gate medium that induces the transient grating in the gate medium.

In a sixth example, there is disclosed a method according to any of the preceding examples, which includes exciting the source with a pulsed excitation beam, and synchronizing said at least one pulsed gate beam to the pulsed excitation beam with an adjustable delay.

In a seventh example, there is disclosed a method according the preceding sixth example, which includes repeating the imaging of light from the source onto the photo-detector array and the collecting of measurements from the photo-detector array of the light imaged onto the photo-detector array for different adjusted delays and combining the measurements collected from the photo-detector array to construct a graph of the light imaged from the source as a function of time since the excitation of the source.

In an eighth example, there is disclosed a method according to any of the preceding examples, which includes imaging light at a first instant in time to form a first image of light from the source on a first region of the photo-detector array by forming a first transient grating at the first instant in time in the gate medium, and then imaging light at a second instant in time to form a second image of light from the source on a second region of the photo-detector array by forming a second transient grating at the second instant in time in the gate medium, and comparing the measurements collected from the photo-detector array of the light imaged onto the photo-detector at the first region to measurements collected from the photo-detector array of the light imaged onto the photo-detector at the second region.

In a ninth example, there is disclosed a method according to the preceding eighth example, which includes splitting a pulsed gate source beam into a first part and a second part, splitting the first part to produce a first gate beam and a second gate beam, and illuminating the gate medium with the first gate beam and the second gate beam at a first crossing angle to produce the first transient grating in the gate medium, and delaying the second part by a selected delay and producing a third gate beam and a fourth gate beam from the delayed second part, and illuminating the gate medium with the third gate beam and the fourth gate beam at a second crossing angle to produce the second transient grating in the gate medium.

In a tenth example, there is disclosed a method according to the preceding eighth example or the ninth example, which includes repeating the imaging of light from the source onto the photo-detector array and the collecting of measurements from the photo-detector array of the light imaged onto the photo-detector array for different adjustable delays between the first instant in time and the second instant in time and the comparing of the measurements collected from the photo-detector array of the light imaged onto the photo-detector array at the first region to measurements collected from the photo-detector array of the light imaged onto the photo-detector array at the second region for different adjusted intervals of time between the first instant in time and the second instant of time, and computing statistics of the measurements.

In an eleventh example, there is disclosed a method according to any of the preceding examples, which further includes disposing a polychromator between the source and the photo-detector array so that the light imaged from the source onto the photo-detector array includes a spectrum.

In a twelfth example, there is disclosed a method according to the preceding eleventh example, wherein the spectrum includes wavelengths of light in the range of ultraviolet to infrared.

In a thirteenth example, there is disclosed a system for measuring light emitted by a source, said system comprising: a photo-detector array for detecting an image of the light emitted by the source; a gate medium disposed between the source and the photo-detector array so that the image of the light from the source is produced on the photo-detector array when a transient grating is produced in the gate medium; and a pulsed gate beam source for producing at least one pulsed gate beam to form the transient grating in the gate medium.

In a fourteenth example, there is disclosed a system according to the preceding thirteenth example, wherein the gate beam source is a femtosecond pulsed laser and the transient grating persists in the gate medium for less than one picosecond so that the measurements collected from the photo-detector array resolve the light imaged from the source with sub-picosecond time resolution.

In a fifteenth example, there is disclosed a system according to any of the preceding examples, which includes at least one beam splitter for splitting a pulsed beam from the gate beam source into two pulsed gate beams that cross each other in the gate medium to form an interference pattern in the gate medium that induces the transient grating in the gate medium.

In a sixteenth example, there is disclosed a system according to any of the preceding examples, which includes a pulsed excitation beam source synchronized to the pulsed gate beam source, and an adjustable delay line for adjusting delay of said at least one pulsed gate beam with respect to the pulsed excitation beam.

In a seventeenth example, there is disclosed a system according to the preceding sixteenth example, wherein the pulsed excitation beam source is a tunable optical parametric amplifier excited by the pulsed gate beam source.

In an eighteenth example, there is disclosed a system according to any of the preceding examples, wherein said at least one pulsed gate beam produces a first transient grating in the gate medium and a first image of the light from the source on the photo-detector array, and which includes a beam splitter and an adjustable delay line for producing another pulsed gate beam delayed by a selected duration of time from said at least one pulsed gate beam gate pulse, said another pulsed gate beam being directed to the gate medium to produce a second transient grating in the gate medium, so that the photo-detector array detects a second image of the light emitted by the source, and the second image of the light emitted by the source is located on a different region of the photo-detector array than the first image of the light emitted by the source.

In a nineteenth example, there is disclosed a system according to the preceding eighteenth example, which includes a first beam splitter for splitting said at least one pulsed gate beam into a first part and a second part, a second beam splitter for splitting the first part to produce a first gate beam and a second gate beam directed to the gate medium at a first crossing angle to produce the first transient grating in the gate medium, and an adjustable delay line for delaying the second part by a selected delay and a third beam splitter for splitting the delayed second part to produce a third gate beam and a fourth gate beam directed to the gate medium at a second crossing angle to produce the second transient grating in the gate medium.

In a twentieth example, there is disclosed a system according to any of the preceding examples, which further includes a polychromator disposed between the source and the photo-detector array so that the light imaged from the source onto the photo-detector array includes a spectrum.

In a twenty-first example, there is disclosed a system according to the preceding twentieth example, wherein the spectrum includes wavelengths of light in the range of ultraviolet to infrared.

The various embodiments described above are provided by way of illustration only and should not be construed to limit the scope of the disclosure. Therefore, many such details are neither shown nor described. Even though numerous characteristics and advantages of the present technology have been set forth in the foregoing description, together with details of the structure and function of the present disclosure, the disclosure is illustrative only, and changes may be made in the detail, especially in matters of shape, size and arrangement of the parts within the principles of the present disclosure to the full extent indicated by the broad general meaning of the terms used in the attached claims. It will therefore be appreciated that the embodiments described above may be modified within the scope of the appended claims. Claim language reciting "at least one of" a set indicates that one member of the set or multiple members of the set satisfy the claim.

The invention claimed is:

1. A method of measuring light emitted by a source, said method comprising:
   (a) imaging light from the source onto a photo-detector array at a selected instant in time by disposing a gate medium between the source and the photo-detector array and also illuminating the gate medium with at least one pulsed gate beam to form a transient grating in the gate medium at the selected instant in time;
   (b) exciting the source with a pulsed excitation beam, and synchronizing at least one pulsed gate beam to the pulsed excitation beam with an adjustable delay;
   (c) collecting measurements from the photo-detector array of the light imaged onto the photo-detector array; and
   (d) repeating the imaging of light from the source onto the photo-detector array and the collecting of measurements from the photo-detector array of the light imaged onto the photo-detector array for different adjusted delays and combining the measurements collected from the photo-detector array to construct a graph of the light imaged from the source as a function of time since the excitation of the source.

2. The method as claimed in claim 1, wherein said at least one pulsed gate beam is produced by a femtosecond pulsed laser and the transient grating persists in the gate medium for less than one picosecond so that the measurements collected from the photo-detector array resolve the light imaged from the source with sub-picosecond time resolution.

3. The method as claimed in claim 1, wherein the pulsed gate beam is chirped to sweep the imaged light from the source across the photo-detector array.

4. The method as claimed in claim 1, wherein the gate medium is configured as an image plate, and the transient grating occupies a fraction of the image plate and sweeps across the image plate.

5. The method as claimed in claim 1, which includes illuminating the gate medium with two or more pulsed gate beams crossing each other in the gate medium to form an interference pattern in the gate medium that induces the transient grating in the gate medium.

6. The method as claimed in claim 1, which includes imaging light at a first instant in time to form a first image of light from the source on a first region of the photo-detector array by forming a first transient grating at the first instant in time in the gate medium, and then imaging light at a second instant in time to form a second image of light from the source on a second region of the photo-detector array by forming a second transient grating at the second instant in time in the gate medium, and comparing the measurements collected from the photo-detector array of the light imaged onto the photo-detector array at the first region to measurements collected from the photo-detector array of the light imaged onto the photo-detector at the second region.

7. The method as claimed in claim 6, which includes splitting a pulsed gate source beam into a first part and a second part, splitting the first part to produce a first gate beam and a second gate beam, and illuminating the gate medium with the first gate beam and the second gate beam at a first crossing angle to produce the first transient grating in the gate medium, and delaying the second part by a selected delay and producing a third gate beam and a fourth gate beam from the delayed second part, and illuminating the gate medium with the third gate beam and the fourth gate beam at a second crossing angle to produce the second transient grating in the gate medium.

8. The method as claimed in claim 6, which includes repeating the imaging of light from the source onto the photo-detector array and the collecting of measurements from the photo-detector array of the light imaged onto the photo-detector array for different adjustable delays between the first instant in time and the second instant in time and the comparing of the measurements collected from the photo-detector array of the light imaged onto the photo-detector array at the first region to measurements collected from the photo-detector array of the light imaged onto the photo-detector array at the second region for different adjusted intervals of time between the first instant in time and the second instant of time, and computing statistics of the measurements.

9. The method as claimed in claim 1, which further includes disposing a polychromator between the source and the photo-detector array so that the light imaged from the source onto the photo-detector array includes a spectrum.

10. The method as claimed in claim 9, wherein the spectrum includes wavelengths of light in the range of ultraviolet to infrared.

11. A system for measuring light emitted by a source, said system comprising:
 (a) a photo-detector array for detecting an image of the light emitted by the source;
 (b) a gate medium disposed between the source and the photo-detector array so that the image of the light from the source is produced on the photo-detector array when a transient grating is produced in the gate medium;
 (c) a pulsed gate beam source for producing at least one pulsed gate beam to form the transient grating in the gate medium;
 (d) a pulsed excitation beam source synchronized to the pulsed gate beam source; and
 (e) an adjustable delay line for adjusting delay of said at least one pulsed gate beam with respect to the pulsed excitation beam.

12. The system as claimed in claim 11, wherein the gate beam source is a femtosecond pulsed laser and the transient grating persists in the gate medium for less than one picosecond so that the measurements collected from the photo-detector array resolve the light imaged from the source with sub-picosecond time resolution.

13. The system as claimed in claim 11, which includes at least one optical element for splitting a pulsed beam from the gate beam source into two or more pulsed gate beams that cross each other in the gate medium to form an interference pattern in the gate medium that induces the transient grating in the gate medium.

14. The system as claimed in claim 11, wherein the pulsed excitation beam source is a tunable optical parametric amplifier excited by the pulsed gate beam source.

15. The system as claimed in claim 11, wherein said at least one pulsed gate beam produces a first transient grating in the gate medium and a first image of the light from the source on the photo-detector array, and which includes an optical element for splitting the gate beam and an adjustable delay line for producing another pulsed gate beam delayed by a selected duration of time from said at least one pulsed gate beam gate pulse, said another pulsed gate beam being directed to the gate medium to produce a second transient grating in the gate medium, so that the photo-detector array detects a second image of the light emitted by the source, and the second image of the light emitted by the source is located on a different region of the photo-detector array than the first image of the light emitted by the source.

16. The system as claimed in claim 15, which includes a first optical element for splitting said at least one pulsed gate beam into a first part and a second part, a second optical element for splitting the first part to produce a first gate beam and a second gate beam directed to the gate medium at a first crossing angle to produce the first transient grating in the gate medium, and an adjustable delay line for delaying the second part by a selected delay and a third optical element for splitting the delayed second part to produce a third gate beam and a fourth gate beam directed to the gate medium at a second crossing angle to produce the second transient grating in the gate medium.

17. The system as claimed in claim 11, which further includes a polychromator disposed between the source and the photo-detector array so that the light imaged from the source onto the photo-detector array includes a spectrum.

18. The system as claimed in claim 17, wherein the spectrum includes wavelengths of light in the range of ultraviolet to infrared.

* * * * *